US011690531B2

(12) United States Patent
Ottley et al.

(10) Patent No.: US 11,690,531 B2
(45) Date of Patent: Jul. 4, 2023

(54) COMPLIANT MULTI-MODE SENSING SYSTEMS AND METHODS

(71) Applicant: Bend Labs, Inc., Salt Lake City, UT (US)

(72) Inventors: Colton A. Ottley, Farmington, UT (US); Jared K. Jonas, Seattle, WA (US); Colin D. Eichinger, Salt Lake City, UT (US)

(73) Assignee: Nitto Bend Technologies, Inc., Farmington, UT (US)

( * ) Notice: Subject to any disclaimer, the term of this patent is extended or adjusted under 35 U.S.C. 154(b) by 249 days.

(21) Appl. No.: 17/061,163

(22) Filed: Oct. 1, 2020

(65) Prior Publication Data

US 2021/0102797 A1 Apr. 8, 2021

Related U.S. Application Data

(60) Provisional application No. 62/909,741, filed on Oct. 2, 2019.

(51) Int. Cl.
*G01B 7/30* (2006.01)
*G01B 7/00* (2006.01)
(Continued)

(52) U.S. Cl.
CPC ............ *A61B 5/1071* (2013.01); *G01B 7/003* (2013.01); *G01B 7/30* (2013.01); *G01D 5/24* (2013.01);
(Continued)

(58) Field of Classification Search
CPC .......... A61B 5/1071; A61B 2562/0247; A61B 2562/0261; A61B 5/6807; A63B 2220/50; G01B 7/003; G01B 7/22; G01B 7/30; G01D 21/02; G01D 5/24; G01D 5/2412; G01L 1/146; G01L 1/205
See application file for complete search history.

(56) References Cited

U.S. PATENT DOCUMENTS 10,317,200 B1   6/2019 Han et al.
2007/0186664 A1  8/2007 Powlesland et al.
(Continued)

FOREIGN PATENT DOCUMENTS

WO   WO2017165809 A1   9/2017

OTHER PUBLICATIONS

International Searching Authority, International Search Report and Written Opinion for Application No. PCT/US2020/053928 dated Feb. 5, 2021.
(Continued)

*Primary Examiner* — Jermele M Hollington
*Assistant Examiner* — Suresh K Rajaputra
(74) *Attorney, Agent, or Firm* — Parsons Behle & Latimer (57) ABSTRACT

Disclosed embodiments include a multi-mode sensor including an elastomeric strand having a first multi-mode sensing region configured to sense at least two different physical parameters, and a second multi-mode sensing region, space apart from the first multi-mode sensing region, and configured to sense at least two different physical parameters. In some disclosed embodiments the first multi-mode sensing region is configured to measure the physical parameters of angular displacement and strain.

26 Claims, 10 Drawing Sheets

(51) Int. Cl.
    *G01D 5/241*     (2006.01)
    *A61B 5/107*     (2006.01)
    *G01L 1/14*     (2006.01)
    *G01D 5/24*     (2006.01)
    *A61B 5/00*     (2006.01)

(52) U.S. Cl.
    CPC ............ *G01D 5/2412* (2013.01); *G01L 1/146* (2013.01); *A61B 5/6807* (2013.01); *A61B 2562/0247* (2013.01); *A63B 2220/50* (2013.01)

(56) References Cited

U.S. PATENT DOCUMENTS

| | | | |
|---|---|---|---|
| 2015/0122044 A1 | 5/2015 | Gianchandani et al. | |
| 2016/0305759 A1* | 10/2016 | Reese | G01B 7/30 |
| 2017/0168567 A1 | 6/2017 | Reese et al. | |
| 2017/0273599 A1* | 9/2017 | Reese | A61B 5/6807 |

OTHER PUBLICATIONS

Patent Office of Spain; Search Report for Application No. 202290016 dated May 17, 2022.

* cited by examiner

COMPLIANT MULTI-MODE SENSING SYSTEMS AND METHODS

CROSS-REFERENCE TO RELATED APPLICATIONS

This application, under 35 U.S.C. § 119, claims the benefit of U.S. Provisional Patent Application Ser. No. 62/909,741 filed on Oct. 2, 2019, and entitled "Compliant Multi-Mode Sensing Systems and Methods," the contents of which are hereby incorporated by reference herein.

This application is also related to the following U.S. Patents, Patent Application Publications, and non-published applications, the contents of which are hereby incorporated by reference herein.

| U.S. Pat. Nos. | U.S. patent application Pub. | U.S. Non-published App. |
| --- | --- | --- |
| 8,941,392 | 2017/0273599 | 15/943,295 |
| 9,222,764 | | |
| 9,476,692 | | |
| 9,612,102 | | |
| 9,874,431 | | |
| 10,551,917 | | |

FIELD OF THE DISCLOSURE

This disclosure relates generally to compliant (i.e., flexible, bendable) sensors. More particularly, this disclosure relates to systems and methods for multi-mode sensing to enable sensing of one or more of angular displacement, strain, stretch, force, pressure, temperature, torsion, or the like, simultaneously or independently of one another.

BACKGROUND

Sensors for detecting, measuring, and monitoring environmental events or changes are ubiquitous in the field of engineering. Sensors may provide a corresponding output responsive to detecting, measuring, and monitoring environmental events or changes. A variety of sensors exist and include temperature sensors, pressure sensors, ultrasonic sensors, strain sensors, light sensors, flex and bend sensors, angular displacement sensors, among others. Sensors may use different types of sense elements, such as capacitive sense elements, resistive sense elements, photonic sense elements, or other types of sense elements, to sense the environmental changes.

It is often desirable for a sensor, or set of sensors, to be able to measure more than one parameter, sometimes in more than one place, at the same time, which is referred to herein as multi-mode. Likewise, it may be desirable to change the mode of operation of a particular sensor or set of sensors. Existing systems and methods for simultaneous or multi-mode sensing are inconvenient and suffer from many drawbacks.

SUMMARY

Accordingly, disclosed embodiments address the above noted, and other, inconveniences and drawbacks of existing systems and methods. Disclosed embodiments include a multi-mode sensor system including a compliant material having a length, a width, a top side, and a bottom side. The sensor system also includes a first electrode embedded in the compliant material adjacent to the bottom side and extending substantially continuously along the length of the compliant material, a first attachment region in the compliant material having a first thickness, and a first sense region in the compliant material located adjacent to the first attachment region and having a second thickness larger than the first thickness and further having a second electrode embedded in the compliant material adjacent to the top side.

Further disclosed embodiments include a second attachment region in the compliant material located adjacent to the first sense region on an opposite side of the first sense region than the first attachment region, the second attachment region having a third thickness smaller than the second thickness.

Further disclosed embodiments include a second sense region in the compliant material located adjacent to the second attachment region and having a second thickness larger than the first and third thickness and further comprising a third electrode embedded in the compliant material adjacent to the top side.

Further disclosed embodiments have the compliant material configured such that a bend within the either of the first or second sense regions induce a strain within at least one of the first or second attachment regions. In further disclosed embodiments the compliant material is an elastomeric matrix.

Also disclosed is a multi-mode sensor system having a first attachment region, a first sense region having a first side located adjacent to the first attachment region, a second attachment region located adjacent to a second side of the first sense region, and a second sense region located adjacent to the second attachment region on another side of the second attachment region.

In further disclosed embodiments the first and second sense region are a first material and the first and second attachment region are a second material different that the first material. In further disclosed embodiments the first material is an elastomeric matrix.

In further disclosed embodiments the first and second sense region include compliant capacitors. In further disclosed embodiments the first and second sense regions are configured to measure different physical parameters. In further disclosed embodiments the first sense region is configured to measure angular displacement and the second sense region is configured to measure force.

Also disclosed is a system for analyzing data relative to sensed parameters, the system including a sensor system configured to sense at least one physical parameter, an interface device further including a user interface, a measurement circuit in communication with the sensor system, and a microcontroller including a calculation circuit in communication with the measurement circuit that calculates and outputs data related to the at least one sensed physical parameter, and a memory comprising control and analysis software in communication with the calculation circuit that analyzes and stores the data related to the at least one sensed physical parameter.

Further disclosed embodiments include a remote device having a display for displaying the data related to the at least one sensed physical parameter.

Further disclosed embodiments include a biofeedback device to provide a user with an indication that a predetermined condition has been reached related to the at least one sensed parameter.

In further disclosed embodiments the sensor system further includes at least one compliant capacitor. In further disclosed embodiments the sensor system further includes a first sense region, and a second sense region. In further disclosed embodiments the first and second sense regions are configured to measure different physical parameters.

In further disclosed embodiments the sensor system further includes a compliant capacitor that communicates changes in capacitance due to deformation to the measurement circuit. In further disclosed embodiments the compliant capacitor is an elastomeric material. In further disclosed embodiments the compliant capacitor measures angular displacement.

Also disclosed is a multi-mode sensor having a first strain transformation structure, a first sensor beneath the first transformation structure, an offset region beneath the first sensor, and a second sensor beneath the offset region. Further disclosed embodiments include a second strain transformation structure beneath the second sensor.

In further disclosed embodiments the first sensor and the second sensor are capacitive sensors. In further disclosed embodiments a differential capacitive measurement between the first sensor and the second sensor measures angular displacement. In further disclosed embodiments an additive capacitive measurement between the first sensor and the second sensor measures force. In further disclosed embodiments an additive capacitive measurement between the first sensor and the second sensor measures strain. In further disclosed embodiments the first sensor and the second sensor are configured to measure different physical parameters.

Further disclosed embodiments include a first axis about which the first transformation structure, the first sensor, the second sensor, and the second transformation structure are substantially aligned, a third strain transformation structure substantially aligned with a second axis that is substantially orthogonal to the first axis, a third sensor adjacent to the third transformation structure and substantially aligned with the second axis, a second offset region adjacent to the third sensor, a fourth sensor adjacent to the second offset region and substantially aligned with the second axis, and a fourth strain transformation structure adjacent to the fourth sensor and substantially aligned with the second axis. In further disclosed embodiments the first sensor, the second sensor, the third sensor, and the fourth sensor are configured to measure different physical parameters.

Further disclosed embodiments include a fifth strain transformation structure substantially aligned with a third axis that is substantially orthogonal to both the first axis and the second axis, a fifth sensor adjacent to the fifth transformation structure and substantially aligned with the third axis, a third offset region adjacent to the fifth sensor, a sixth sensor adjacent to the third offset region and substantially aligned with the third axis, and a sixth strain transformation structure adjacent to the sixth sensor and substantially aligned with the third axis. In further disclosed embodiments the first sensor, the second sensor, the third sensor, the fourth sensor, the fifth sensor, and the sixth sensor are configured to measure different physical parameters.

Also disclosed is a multi-mode sensor having an elastomeric strand including a first multi-mode sensing region configured to sense at least two different physical parameters, and a second multi-mode sensing region, space apart from the first multi-mode sensing region, and configured to sense at least two different physical parameters. In further disclosed embodiments the first multi-mode sensing region is configured to measure the physical parameters comprising angular displacement and strain. Other embodiments, advantages, efficiencies, and features also exist.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

It should also be understood that, as used herein, the terms "vertical," "horizontal," "lateral," "upper," "lower," "left," "right," "inner," "outer," etc., can refer to relative directions or positions of features in the disclosed devices and/or assemblies shown in the Figures. For example, "upper" or "uppermost" can refer to a feature positioned closer to the top of a page than another feature. These terms, however, should be construed broadly to include devices and/or assemblies having other orientations, such as inverted or inclined orientations where top/bottom, over/under, above/below, up/down, and left/right can be interchanged depending on the orientation.

Embodiments of the present disclosure address the deficiencies described above and other deficiencies by providing a multi-region angular displacement sensor that includes multiple sense regions (also referred to as "sensing regions) that are spatially distinct. A sense region may include an angular displacement unit used to determine an angular displacement associated with the particular sense region.

The angular displacement of a sense region may be determined independent of an angular displacement of another sense region of the multi-region angular displacement sensor. The angular displacement unit is stretchable between a first end and a second end and bendable along a length of the first angular displacement unit and the length of the multi region angular displacement sensor in any direction in three-dimensional space.

In one embodiment, the multi-region angular displacement sensor may be connected to a strand of compliant material (also referred to as "strand", "body", "elongated body") with a center axis orientated along a length of the strand and orientated perpendicular to a width of the strand when the strand is in a linear and non-bent position. The strand may be stretchable along the length of the strand and may be bendable along the length of the strand in any direction in three-dimensional space. The strand may be of an elastomeric material such as rubber. The strand may include multiple sense regions. A sense region may be an area defined by an angular displacement unit or other sense unit within a sense region of the strand. An angular displacement unit may include one or more compliant capacitors offset from the center axis of the strand, where the compliant capacitors are connected to (e.g., connected on top of partially embedded in, or fully embedded in) the strand (e.g., compliant matrix). The compliant capacitors may extend along a line offset from part of the center axis, where the part of the center axis may be the angular displacement axis for the respective angular displacement unit. A first sense region may include a first angular displacement unit. The first angular displacement unit includes a first end defining a first vector and a second end defining a second vector. An angular displacement between the first vector and the second vector within a first plane extending along the first part of the center axis and orthogonal to the width of the first angular displacement unit may be determined responsive to deformation of the first angular displacement unit. A deformation may refer to any change in size or shape of an object, Such as an angular displacement unit, due to an applied force from another object. The deformation energy may be transferred through work rather than by heat, chemical reaction, moisture, etc. In one example, the deformation may be from a tensile force (e.g., pulling), a compressive force (e.g., pushing), shear force, bending force, and/or torsional force (e.g., twisting). The first angular displacement unit may be stretchable between the first end and the second end and bendable along a length of the first angular displacement unit in any direction in a three-dimensional space. Other sense regions of the multiple sense regions may include an angular displacement unit similar to the first angular displacement unit described above. Each angular displacement unit of the respective sense region may measure angular displacement of the respective sense region independent from other sense regions. In one example, the multi-region angular displacement sensor may be used to measure the angular displacement of joints of a human body to determine movement. For example, the multi-region angular displacement sensor may be used to measure the angular displacement of joints of a human hand to determine the movement of the human hand.

Figure 1:
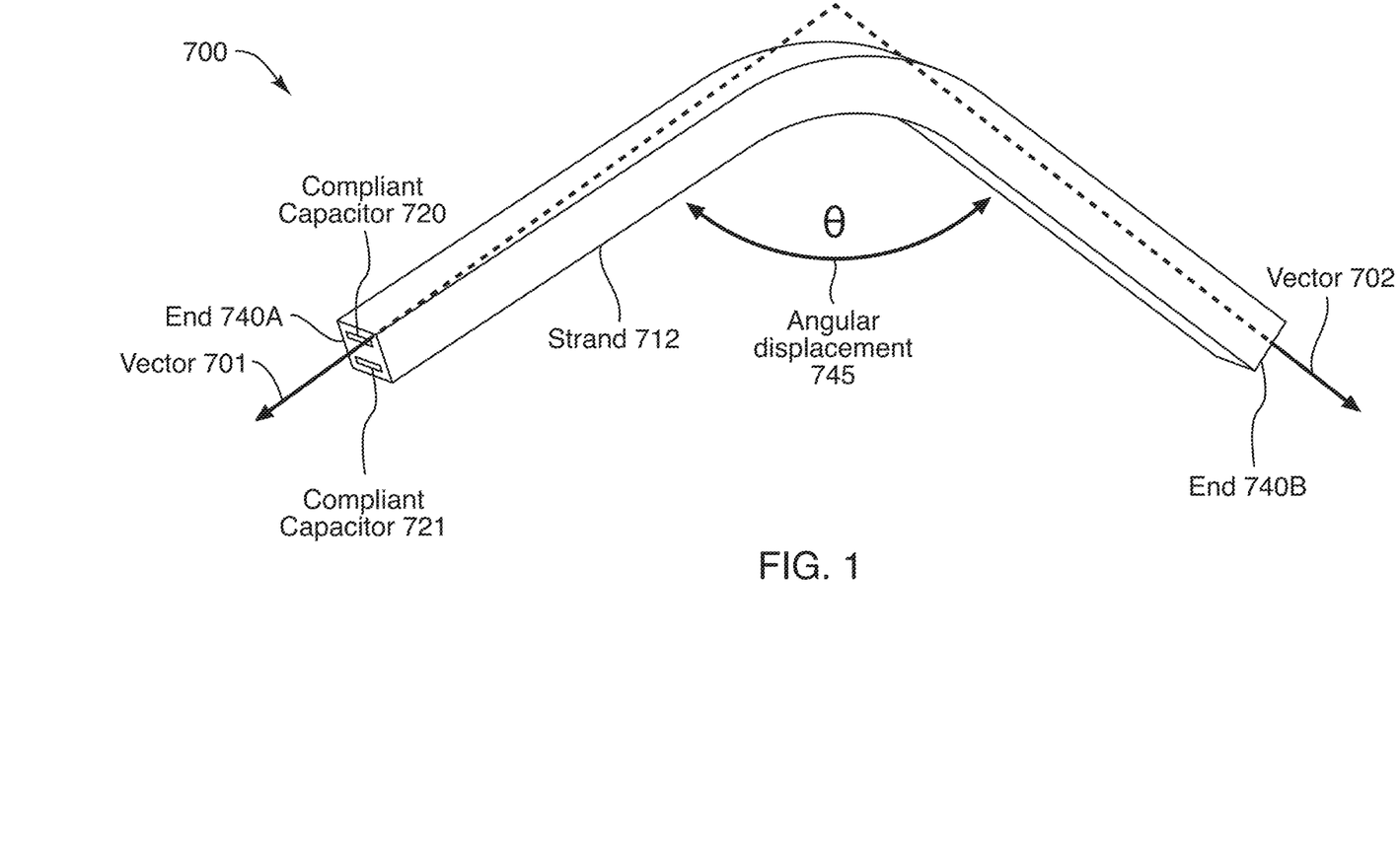
FIG. 1 is a schematic illustration of a perspective view of an angular displacement unit in accordance with disclosed embodiments.

FIG. 1 illustrates a perspective view of an angular displacement unit, according to some embodiments. In one embodiment, angular displacement unit 700 may be an angular displacement unit, as described herein. In another embodiment, angular displacement unit 700 may be angular displacement sensor (e.g., a single sense region angular displacement sensor). Angular displacement unit 700 illustrates a strand 712 of compliant material. Embedded in the strand 712 are compliant capacitor 720 and compliant capacitor 721 that are offset about a center axis (which is approximately where vector 701 and 702 are located). Vector 701 is located at end 740A of angular displacement unit 700. Vector 702 is located at end 740B of angular displacement unit 700. Vector 701 and 702 are used to measure angular displacement 745 (θ). Although two compliant capacitors are illustrated, one or more compliant capacitors may be implemented. Compliant capacitor 720 (and compliant capacitor 721) has two compliant electrodes separated by a compliant dielectric. Other electrode configurations may also be used. Additionally, additional placements of compliant capacitors may also be used. It should be appreciated that additional compliant capacitors may be implemented to measure angular displacement along any number of additional places of measurement.

Figure 2:
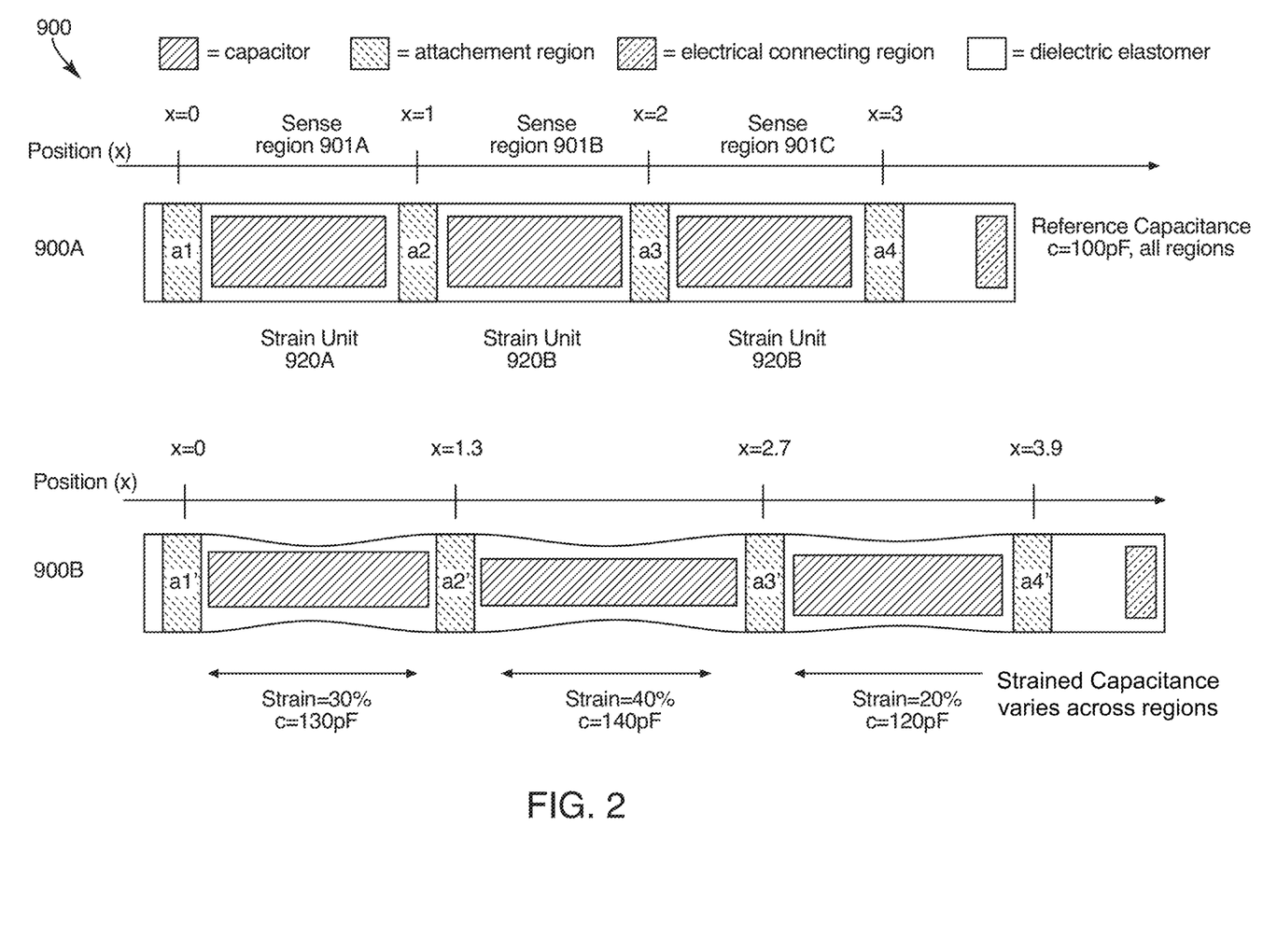
FIG. 2 is a schematic illustration of a multi-region strain sensor in accordance with disclosed embodiments.

FIG. 2 is an illustration of a multi-region strain sensor, in accordance with disclosed embodiments. Multi-region strain sensor 900 may include similar features as multi-region angular displacement sensor, unless otherwise described. Multi-region strain sensor 900 includes multiple sense regions 901 including sense region 901A, 901B, and 901C. Each sense region 901 includes a strain unit 920 (e.g., stretch sensor). Sense region 901A includes strain unit 920A, sense region 901B includes strain unit 920B, and sense region 901C includes strain unit 920B. Strain units 920 are compliant and deform similarly to an angular displacement unit. Strain units 920 may measure strain responsive to a tensile force (e.g., stretch).

Each sense region 901 may include one or more sense elements, such as a compliant capacitor, and may sense strain independently. Sense region 901 may deform proportionally to the applied strain. In some embodiments, attachment regions (e.g., a1-a4) are located between the one or more sense elements. Attachment regions of multi-region strain sensor 900 may be similar to the attachment regions described with respect to multi-region angular displacement sensor described herein. In another embodiment, attachment regions may be located on top of the sense elements. The attachment regions may provide an attachment point to which the multi-region strain sensor 900 may be secured to a surface. In one embodiment, the attachment region of multi-region strain sensor 900 may have limited or no elasticity, so that tensile force may be imparted to strain units 920. Once attached, the attachment region may provide a boundary so that a load may be applied, and strain induced on a sense element. For example, a sense element may lie over a joint and an attachment region may be secured at a position above the joint and another attachment region may be secured below the joint. When the joint flexes, the flex induces a strain on the sense element, rather than in the attachment region. The attachment region may be made of any material, such as non-conducting elastomer or another non-conducting material. The attachment region may be secured to another surface by any material, such as glue, a staple, compression, or thread-like material. The multi-region strain sensor 900A illustrates the sense elements in a state of negligible strain. Multi-region strain sensor 900B illustrates the sense elements under different amounts of strain (e.g., 30%, 40%, and 20%). The percentage of strain is an indication of the amount of deformation (i.e., change in area) of each sense element from a negligible strain state to a strained state. A change in distance between the attachment regions induces a strain within the sense element. For example, if the reference capacitance (no deformation) for each sense region 901 is 100 pF, the capacitance resulting from the applied strain (shown as x values on the axis on the top of multi-region strain sensor 900) may result in a proportional increase in capacitance for each sense element. Although multi-region strain sensor 900 illustrates a multi-region strain sensor with three sense regions 901, it should be appreciated that multi-region strain sensor may have any number of sense regions 901. It should also be appreciated that a multi-region sensor may include one or more sense regions with angular displacement units, one or more sense regions with strain units, and/or any one or more sense regions with other types of sense units.

Figure 3:
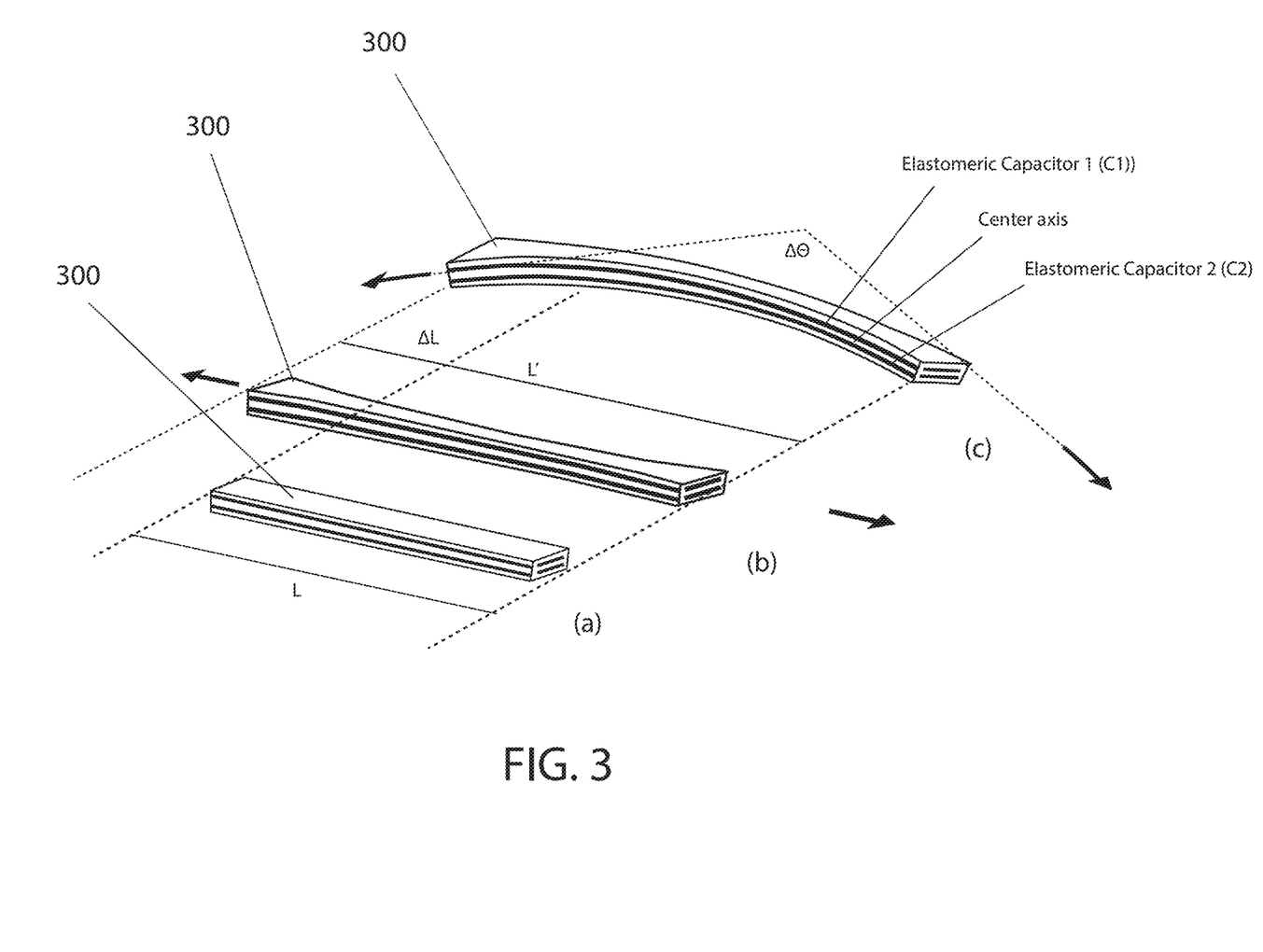
FIG. 3 is a schematic illustration of measurements of stretching and simultaneous or independent bending and stretching/straining in accordance with disclosed embodiments.

FIG. 3 is schematic illustrations of measurements of stretching and simultaneous or independent bending and stretching/straining in accordance with disclosed embodiments. As shown in FIG. 3 embodiments of a multi-mode sensor 300 are capable of independently, or simultaneously, measuring angular displacement, strain, stretch, force, pressure, or the like. As discussed in more detail with reference to FIG. 8, each multi-mode sensors 300 may comprise one or more strain transformation structures, one or more capacitors, strain sensors, resistive sensors, pressure sensors, or other parameter sensors, offset from each other. As shown at FIG. 3(a) a multi-mode sensor 300 with Length (L) in an unstrained and unbent conformation. As shown at FIG. 3(b) the sensor 300 is under linear strain (ΔL) with new Length (L'). As shown at FIG. 3(c) the sensor 300 is under both linear strain (ΔL) with new Length (L') and angular displacement ΔΘ where the same sensor 300 is measuring both linear displacement and angular displacement simultaneously. Other embodiments include a multi-mode sensor 300 with multiple axes of bending and/or stretching including 2 or 3 axis angular displacement, that can simultaneously or independently measure bending, strain, pressure, force, and the like.

In general, path independent bending is measured via Capacitor C1−Capacitor C2 and bend independent stretch is measured via Capacitor C1+Capacitor C2. Or, more generally, a differential measurement between sensors for bending and an additive measurement between sensors for force/strain. Other operations are also possible. These operations can be achieved via hardware or software as disclosed herein. Additionally, this arrangement doubles the sensitivity to stretch in the same volume compared to a typical stretch sensor.

Exemplary use cases for Bend+Stretch sensing include: measuring volume of an extensible object (e.g., knowing the radius of curvature and length/stretch allows one to accurately measure volumetric changes of an extensible object). Other uses are also possible.

The same technique can be applied to pressure/force sensors. This arrangement of a force sensor provides a benefit in having a force measurement that is decoupled from bending in the sensor. Traditional force sensing resistors ("FSRs") suffer from error signal induced by bending. Additional discussion is provided in connection with FIG. 7 below.

Figure 4:
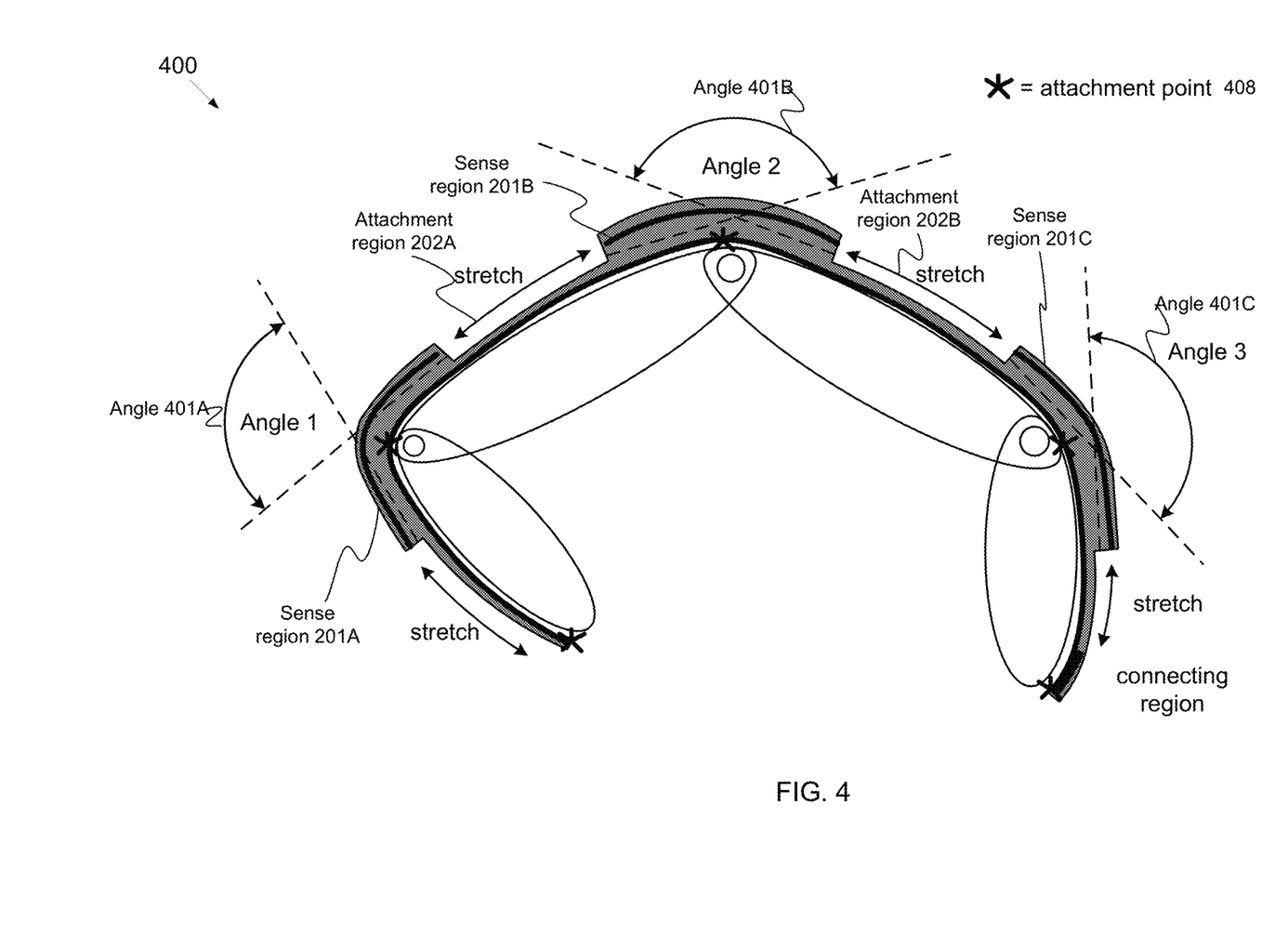
FIG. 4 is a schematic illustration of a multi-region angular displacement sensor in accordance with disclosed embodiments.

FIG. 4 illustrates an application of a multi-region angular displacement sensor, in accordance with some embodiments. For purposes of illustration, and not for limitation, the application of multi-region angular displacement sensor 400 illustrated in FIG. 4 is a schematic illustration of part of a glove (for a hand) where one or more fingers may contain one or more multi-region angular displacement sensors. It should be appreciated that multi-region angular displacement sensor 400 may be used in multiple applications to sense angular displacement. Any of the multi-region angular displacement sensors described herein may be used as multi-region angular displacement sensor 400. FIG. 4 illustrates a single finger. However, it should be appreciated that one or more multi-region angular displacement sensor 400 (with or without stretching regions) may be applied to some or all the joints of an entire hand.

Multi-region angular displacement sensor 400 shows three different angular displacement angles 401 (i.e., angle 401A, angle 401B, and angle 401C), that define the angular orientation of the four ellipsoidal rigid bodies which are schematic representations of parts of a human hand (e.g., a bent finger). When the angles 401 are non-zero they will induce a curvature within the sense regions 201 and induce a strain (e.g., stretch) within the attachment regions 202. As the angles 401 are increased, the length of the attachment regions 202 along the top of the ellipsoidal rigid bodies will also increase. Attachment regions 202 are illustrated as stretching regions. In other embodiments, some or all of attachment regions 202 may not be stretching regions. Since the sense regions 201 are stiffer than the attachment regions 202, the sense regions 201 will deform primarily in curvature by bending, while the increase in length will be facilitated by the attachment regions 202. In one embodiment, the multi-region angular displacement sensor 400 with attachment regions 202 may be attached to the linked ellipsoidal rigid bodies at the five attachment points 408 designated with an asterisk (*). The attachment points 408 may help maintain the position of the sense regions 201 over the curved joint and help transmit the stretch to the attachment region 202. For example, the attachment points 408 may connect to an underlying glove beneath the multi-region angular displacement sensor 400. It should be appreciated than the attachment points 408 may be implemented any number of ways, such as by an adhesive substrate that sticks to the underlying ellipsoidal rigid bodies, may be a band that fits around the ellipsoidal rigid bodies. In some embodiments, no attachment points are implemented. In other embodiments, the same, fewer, or more attachment points are implemented. For each sense region 201, an angular displacement (i.e., angle 401A, angle 401B, and angle 401C), may be measured as a function of the change in capacitance, where the angular displacement is the angle between two vectors defined by the ends of the sense region 201 (e.g., angular displacement unit of the sense region 201). The angular displacement of each sense region 201 may be determined independent from the other sense regions. The sense element (e.g., compliant capacitor) is shown as a thick black line on the upper surface of multi-region angular displacement sensor 400, the traces are shown as a black line on a lower surface of multi-region angular displacement sensor 400, the strand of compliant material is gray, and the linked ellipsoidal rigid bodies are below the multi-region angular displacement sensor 400. In one example, the attachment region 202 may be made of the same material as the strand of compliant material, such as an elastomeric matrix, and/or be a different thickness from strand of compliant material the sense regions 201. In another example, the material of attachment region 202 may be a different material from the sense region 201 of multi-region angular displacement sensor 400, such as Spandex or other elastic material.

Figure 5:
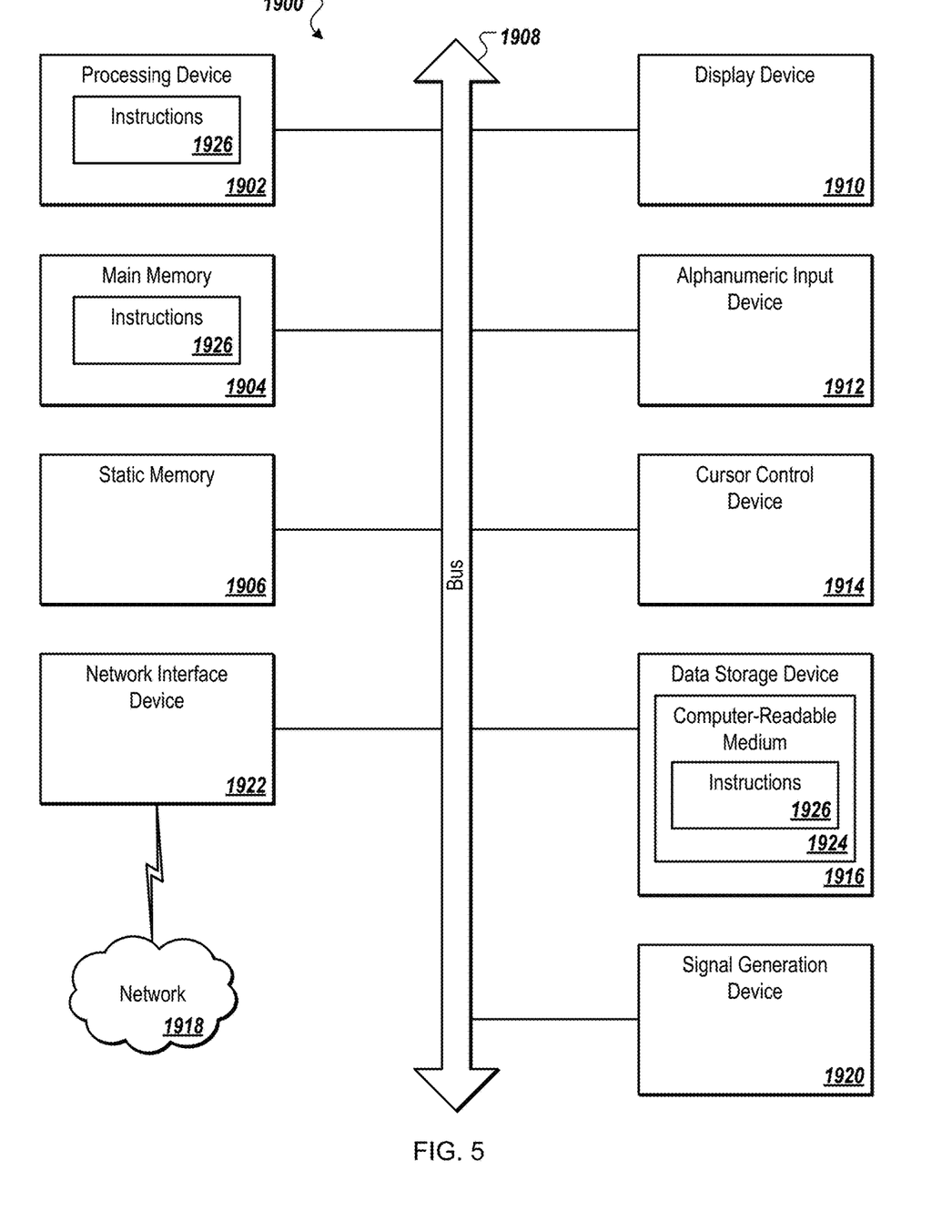
FIG. 5 is a diagrammatic representation of a machine in the example form of a computer system in accordance with disclosed embodiments.

FIG. 5 illustrates a diagrammatic representation of a machine in the example form of a computer system, in accordance with some embodiments. The computer system 1900 may access a set of instructions that when executed cause the machine to perform any one or more of the methodologies discussed herein. The computer system 1900 may correspond to the interface device 20, remote device 22, or micro-controller 115 that executes the control and analysis software 124 of FIG. 6. The computer system 1900 may correspond to an inertial measurement unit (IMU) or a computer system in communication with an IMU, as described herein. In some embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computer system 1900 includes a processing device 1902, a main memory 1904 (e.g., read-only memory (ROM), flash memory, dynamic random access memory (DRAM) such as synchronous DRAM (SDRAM), a static memory 1906 (e.g., flash memory, static random access memory (SRAM), etc.), and a secondary memory 1916 (e.g., a data storage device), which communicate with each other via a bus 1908.

The processing device 1902 represents one or more general-purpose processors such as a microprocessor, central processing unit, or the like. The term "processing device" is used herein to refer to any combination of one or more integrated circuits and/or packages that include one or more processors (e.g., one or more processor cores). Therefore, the term processing device encompasses a microcontroller, a single core CPU, a multi-core CPU and a massively multi-core system that includes many interconnected integrated circuits, each of which may include multiple processor cores. The processing device 1902 may therefore include multiple processors. The processing device 1902 may include a complex instruction set computing (CISC) microprocessor, reduced instruction set computing (RISC) microprocessor, very long instruction word (VLIW) microprocessor, processor implementing other instruction sets, or processors implementing a combination of instruction sets. The processing device 1902 may also be one or more special-purpose processing devices such as an application specific integrated circuit (ASIC), a field programmable gate array (FPGA), a digital signal processor (DSP), network processor, or the like.

The computer system 1900 may further include one or more network interface devices 1922 (e.g., NICs). The computer system 1900 also may include a video display unit 1910 (e.g., a liquid crystal display (LCD) or a cathode ray tube (CRT)), an alphanumeric input device 1912 (e.g., a keyboard), a cursor control device 1914 (e.g., a mouse), and a signal generation device 1920 (e.g., a speaker).

The secondary memory 1916 may include a machine-readable storage medium (or more specifically a computer readable storage medium) 1924 on which is stored one or more sets of instructions 1954 embodying any one or more of the methodologies or functions described herein. The instructions 1954 may also reside, completely or at least partially, within the main memory 1904 and/or within the processing device 1902 during execution thereof by the computer system 1900; the main memory 1904 and the processing device 1902 also constituting machine-readable storage media.

While the computer-readable storage medium 1924 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine that cause the machine to perform any one or more of the methodologies of the present embodiments. The term "computer-readable storage medium" shall accordingly be taken to include, but not be limited to, non-transitory media such as solid-state memories, and optical and magnetic media.

The modules, components and other features described herein can be implemented as discrete hardware components or integrated in the functionality of hardware components such as ASICS, FPGAs, DSPs or similar devices. In addition, the modules can be implemented as firmware or functional circuitry within hardware devices. Further, the modules can be implemented in any combination of hardware devices and software components, or only in software.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "identifying," "measuring," "establishing," "detecting," "modifying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present disclosure also relate to an apparatus for performing the operations herein. This apparatus may be specially constructed for the required purposes, or it may comprise a general purpose computer system selectively programmed by a computer program stored in the computer system. Such a computer program may be stored in a computer readable storage medium, Such as, but not limited to, any type of disk including floppy disks, optical disks, CD-ROMs, and magnetic-optical disks, read only memories (ROMs), random access memories (RAMs), EPROMs, EEPROMs, magnetic disk storage media, optical storage media, flash memory devices, other type of machine accessible storage media, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear as set forth in the description above. In addition, the present embodiments are not described with reference to any particular programming language. It will be appreciated that a variety of programming languages may be used to implement the teachings of the embodiments as described herein.

Figure 6:
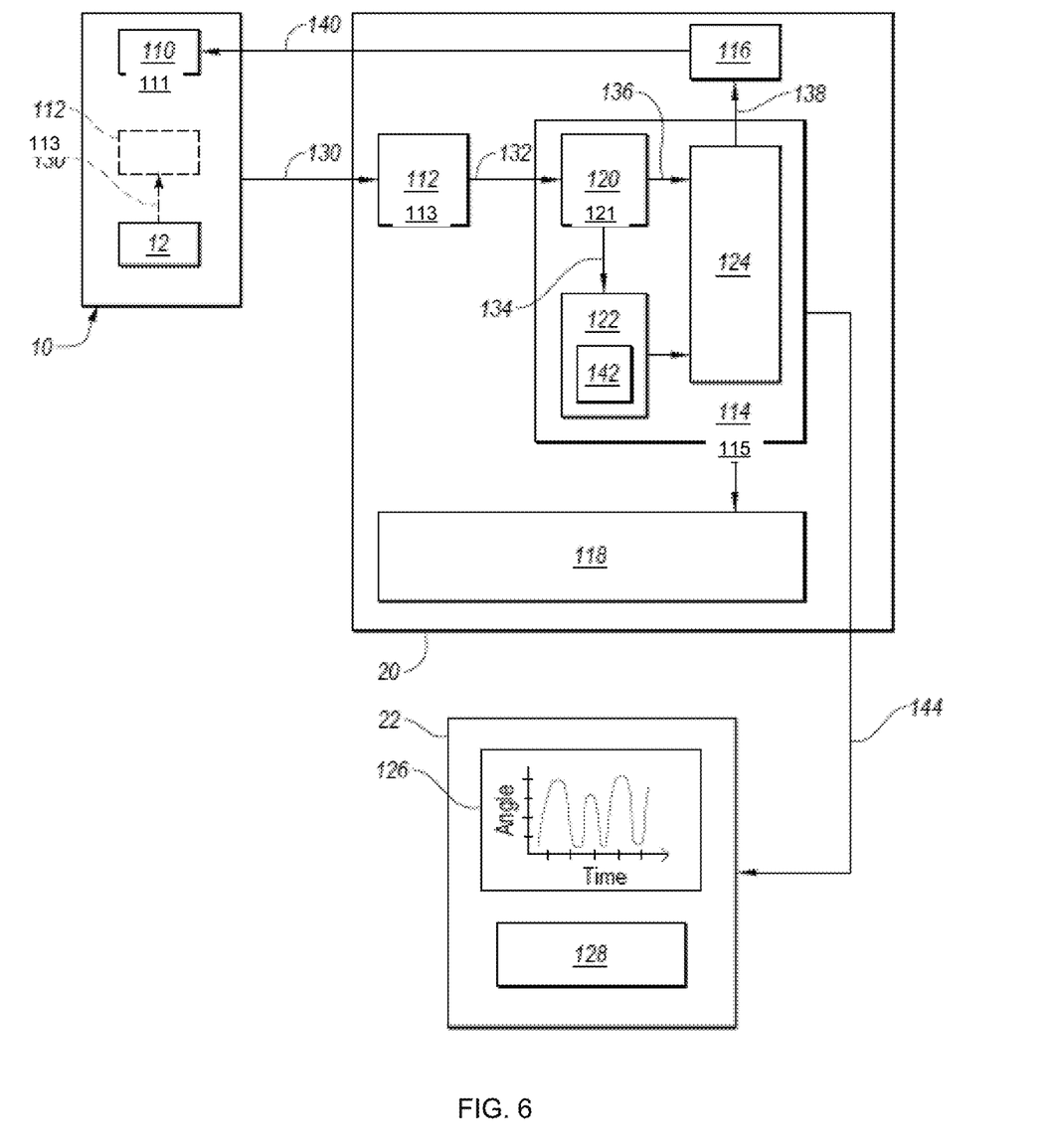
FIG. 6 illustrates a schematic diagram of various components of a system for analyzing data relative to angular displacement, according to disclosed embodiments.

FIG. 6 illustrates a schematic diagram of various components of a system for analyzing data relative to angular displacement, according to disclosed embodiments. In one embodiment, the primary components may include the sensor system 10 (e.g., multi-region angular displacement sensor and/or multi-region strain sensor), the interface device 20 (all or part also referred to as circuit device), and the remote device 22. The sensor system 10 may include the angular displacement unit 12 (e.g., a single angular displacement unit or one or more angular displacement units of a multi-region angular displacement sensor described herein) and a biofeedback device 111. The interface device 20 may include a capacitance measurement circuit 113, a microcontroller 115, a biofeedback amplifier 116, and a user interface 118. The micro-controller 115 may include a calculation circuit 121, a memory 122, and control and analysis software 124. The remote device 22 may include a display 126 and user input 128, and may include the processors and computing devices of for example, a smart phone or personal computer, as known in the art. In other embodiments, the micro-controller 115 may include both analog and digital circuitry to perform the functionality of the capacitance measurement circuit 113, the calculation circuit 121, and biofeedback amplifier 116. In some embodiments, interface device 20 may be a processing device, such as a microprocessor or central processing unit, a controller, special-purpose processor, digital signal processor (DSP), an application specific integrated circuit (ASIC), a field programmable gate array ("FPGA"), or one or more other processing devices known by those of ordinary skill in the art.

In use, for example, upon bending movement of the angular displacement unit 12, the capacitance measurement circuit 113 measures capacitances of the compliant capacitors (e.g., 720, 721) of the angular displacement unit 12. As illustrated in FIG. 6, the capacitance measurement circuit 113 can be housed in the interface device 20 and coupled to the angular displacement unit 12 via wires, as indicated by arrow 130. Alternatively, the capacitance measurement circuit 113 may be housed adjacent to or with the angular displacement unit 12 itself (as indicated with dashed arrow 130') or within, for example, one of the first and second rigid members (not shown) coupled to the angular displacement unit 12. It should be noted that the capacitance measurement circuit 113 can measure capacitance between the at least two electrodes of one of the compliant capacitors. In another embodiment, the capacitance measurement circuit 113 can measure a differential capacitance of the two compliant capacitors. When the angular displacement unit 12 includes the single compliant capacitor the capacitance measurement circuit 113 can measure a single capacitance between the electrodes of the single compliant capacitor. The capacitance measurement circuit 113 can measure the capacitance(s) or differential capacitance in terms of voltage or current. The capacitance measurement circuit 113 then transmits voltage data or current data to the micro-controller 115, such as to the calculation circuit 121, as indicated by arrow 132. The calculation circuit 121 calculates the values of the voltage data or current data provided by the capacitance measurement circuit 113 to calculate the angular displacement 60 between the first and second vectors (e.g., 701, 702). The calculation circuit 121 may then transmit angle data to the memory 122 (which then becomes logged data) and the control and analysis software 124, as indicated by respective arrows 134, 136. In one embodiment, parameters may be input as maximum/minimum limits for angular displacement through, for example, the user interface 118. The user interface 118 may include a display and/or a user input, such as input keys. The maximum limits (and minimum limits) may be useful for a user to know once the user has reached a particular angular displacement with the sensor system 10. As such, if the user does meet the desired parameters (or undesired as the case may be), the control and analysis software 124 may transmit a signal to the biofeedback amplifier 116, as indicated by arrow 138, which in turn may transmit a signal back to the biofeedback device 111, as indicated by arrow 140, at the sensor system 10.

The biofeedback device 111 may then produce a notification to the user that a predefined input parameter has been reached, such as the maximum angular displacement, so that the user understands in real-time the limits relative to the movement of the user's particular joint being analyzed, for example. The notification may be at least one of a visual notification, an audible notification, and a tactile notification or some other notification to facilitate the user's understanding of the user's maximum limit. Alternatively, the notification can be any combination of visual, audible and tactile notifications. The visual notification may be in the form of a blinking (or various colored) light or the like displayed on the sensor system 10 itself or the interface device 20 and/or also may be visualized on a display of the interface device 20. The audible notification may be a ring or beep or the like that may preferably be audibly transmitted from the interface device 20 but may also be transmitted from the sensor system 10. The tactile notification may be coupled to or integrated with one or more rigid members (not shown) of the sensor system 10 or may be integrated in the interface device 20. Such tactile notification may be in the form of a vibration or some other tactile notification, such as a compression member. In this manner, the biofeedback device 111 may notify the user in real time upon extending or contracting one's anatomical joint at a maximum angular displacement according to a predetermined input parameter. Similarly, in another embodiment, a user may input parameters of a minimum angular displacement into the interface device 20 for biofeedback notification. Further, in another embodiment, the user may input parameters for both a minimum angular displacement and a maximum angular displacement. Inputting such parameters may be useful for exercises during physical therapy and for athletes training to obtain particular movements at various anatomical joints.

Upon completing a session of rehabilitation therapy or training or the like, for example, logged data 142 may be stored in the memory 122 or storage device of the interface device 20. Such logged data 142 may also be viewable on the interface device 20 on a display at the user interface 118. The logged data 142 may then be transferred to the remote device 22, as indicated by arrow 144. The remote device 22 may be any known computing device, such as a mobile device, smart phone, tablet, personal computer, gaming system, etc. In one embodiment, the logged data 142 may be transferred to a smart phone by, for example, wireless technology (e.g., over a wireless local area network (WLAN) such as a Bluetooth network or Wi-Fi network) or transferred via mini-USB ports or the like, as known to one of ordinary skill in the art. In another embodiment, the logged data 142 may be transferred to a personal computer via a port, such as a USB port with, for example, a portable memory device, such as a thumb drive. The user may then save the logged data 142 on the remote device 22 for further analysis. As previously set forth, the user may save several sessions of logged data 142 to the remote device 22 to obtain further analysis and comparison data to better understand, for example, progress or regress in the user's angular displacement of the user's anatomical joints.

Although not illustrated, the elements described in FIG. 6 may be powered by numerous power sources that include one or more of batteries, rechargeable batteries, wired power, capacitive storage, and power scavenging techniques, such as radio frequency (RF) power scavenging, among others.

Figure 7:
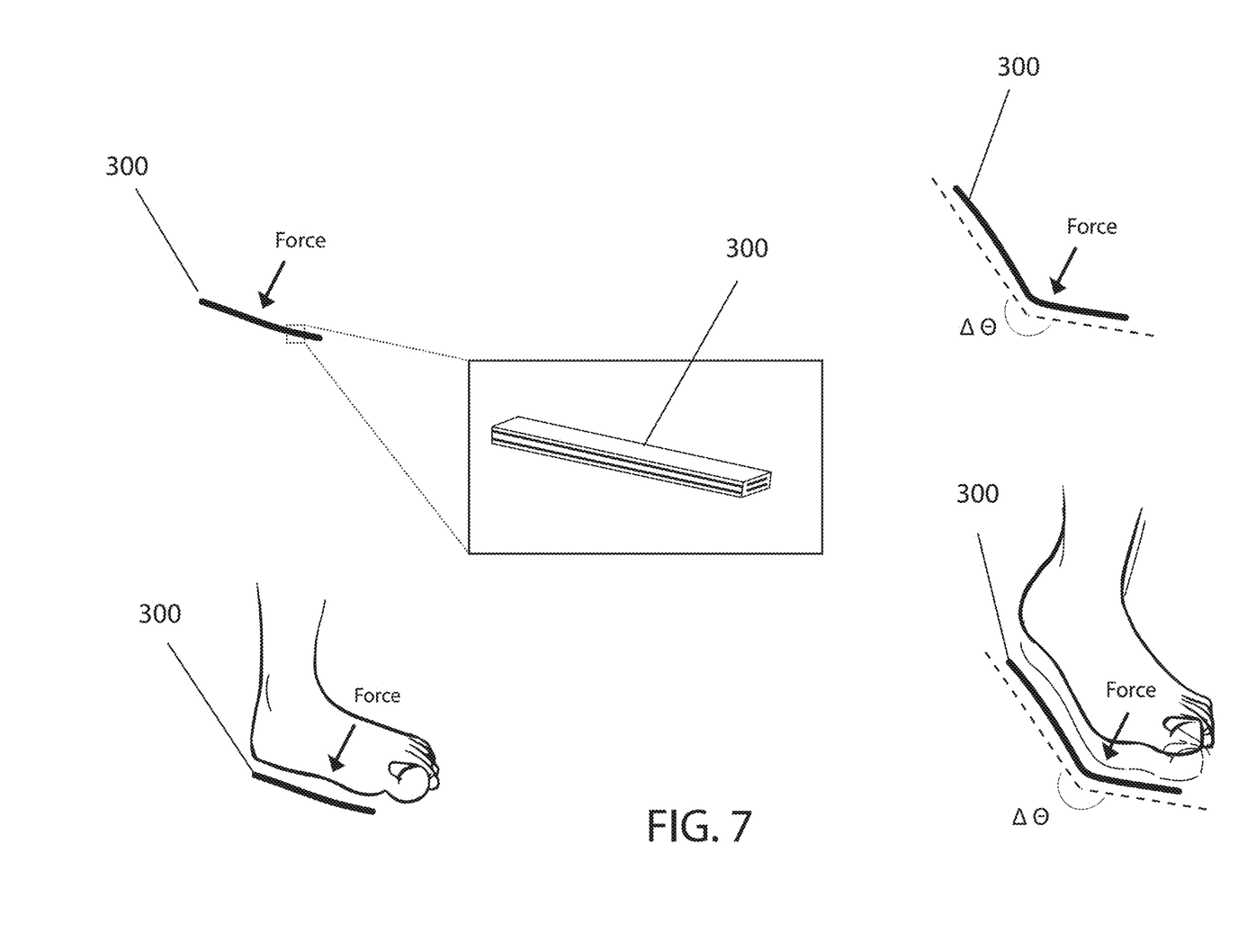
FIG. 7 is a schematic illustration of simultaneous or independent measurements of bending and force in accordance with disclosed embodiments.

FIG. 7 is a schematic illustration of simultaneous or independent measurements of bending and force in accordance with disclosed embodiments. As shown in the illustrations, embodiments of the disclosed multi-mode sensors 300 are able to measure (clockwise from top left) an exerted force on the sensor 300, an amount of bending ($\Delta\Theta$) of the sensor 300 while also measuring a force, the downward force of a foot on the sensor 300 while simultaneously being able to measure the angular displacement (bending ($\Delta\Theta$)), and the downward force of a foot on the sensor 300. Other configurations and measurements are also possible.

Figure 8A:
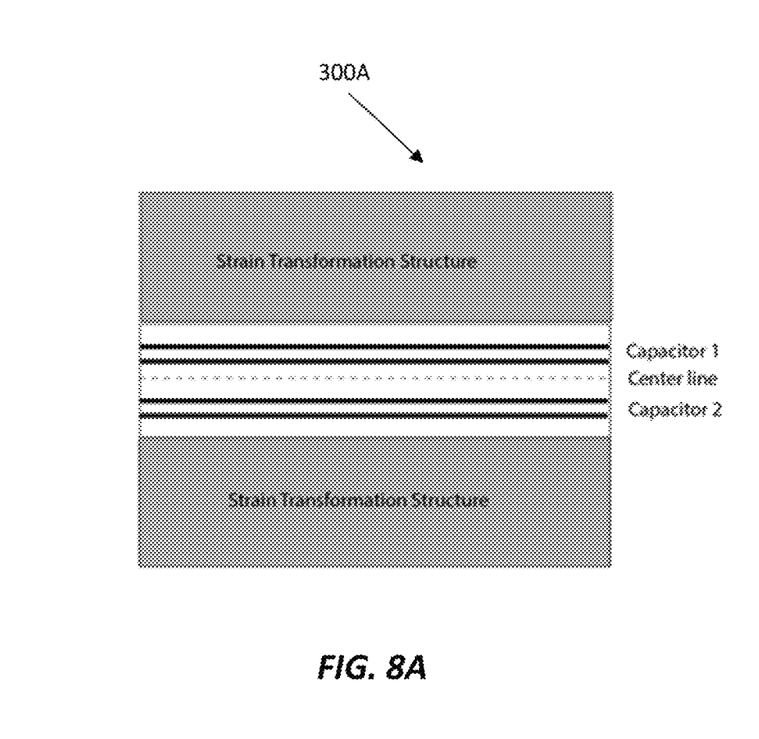
FIGS. 8A-8B are schematic illustrations of multi-mode sensor cross sections including strain transformation structures for increased force/pressure sensitivity in accordance with disclosed embodiments.
Figure 8B:
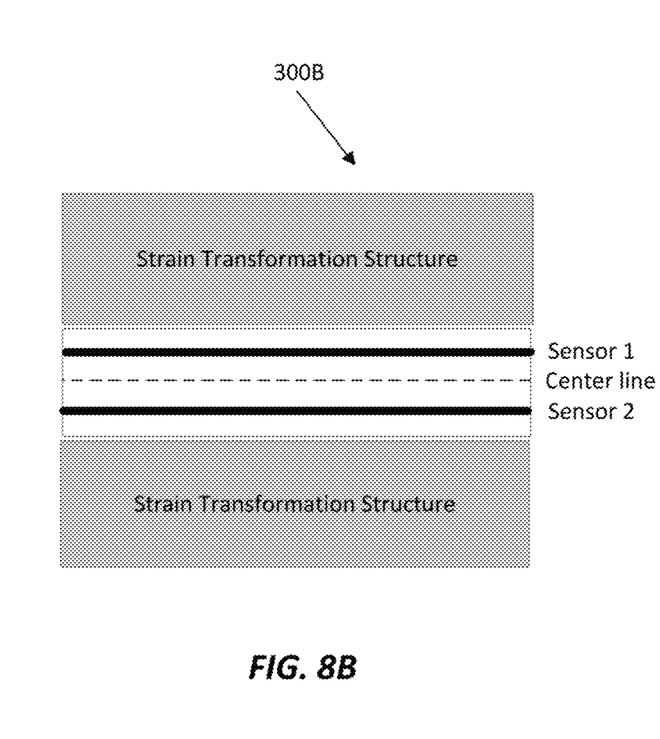

FIGS. 8A-8B are schematic illustrations of a multi-mode sensor (300A, 300B) cross sections including strain transformation structures for increased force/pressure sensitivity in accordance with disclosed embodiments. Additional details of these embodiments can be found in U.S. Pat. App. Pub. 2017/0273599 which is hereby incorporated by reference in its entirety. In general, the strain transformation structures may comprise elastomeric, or other, substances that, among other things, help direct, amplify, or dampen, the force applied to the sensors. As shown in FIG. 8A a multi-mode sensor 300A may comprise a first capacitor (Capacitor 1) and a second capacitor (Capacitor 2) offset from each other about a center line. Such an embodiment may be used, as disclosed herein, to sense angular displacement (bending) as well as force/strain by differential and additive measurements of the various measured capacitances. As shown in FIG. 8B, other embodiments of multi-mode sensors 300B may include other sensors (e.g., sensor 1, sensor 2) such as resistive sensors, FSRs, pressure sensors, or the like, to sense other parameters as disclosed herein. Additionally, other embodiments may include a multi-mode sensor (e.g., 300A, 300B) with a single strain transformation structure on one side. Further, if sensing in multiple axes and directions is desired, a box-like multi-mode sensor may be used with strain transformation structures and sensors on four sides for two axis sensing, or on all six faces of a cube with corresponding sensors for three axis sensing. Other embodiments are also possible.

Figure 9:
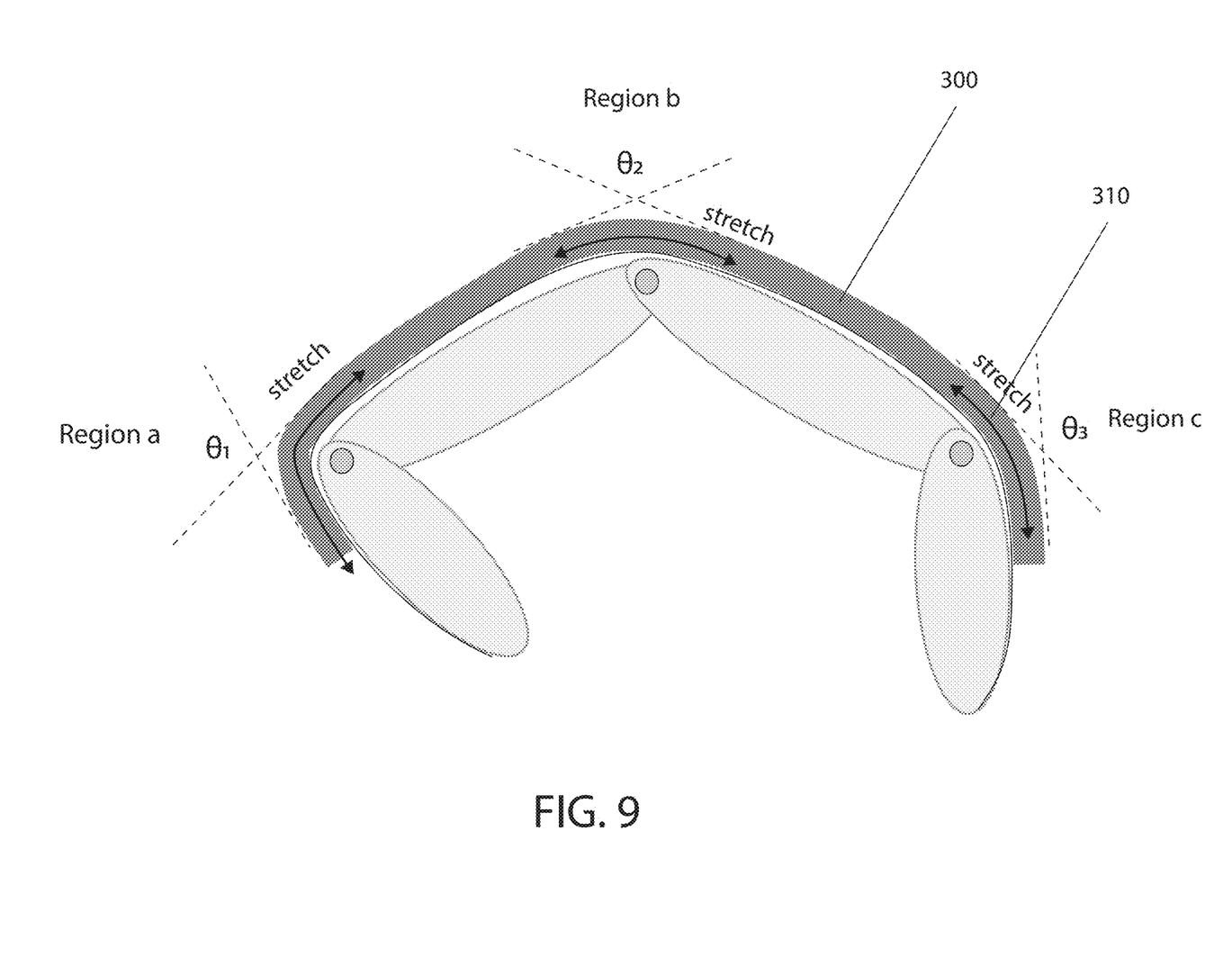
FIG. 9 is a schematic illustration of embodiments of multi-mode sensors that contain multiple regions of sensing whereby each region is capable of multi-mode sensing in accordance with disclosed embodiments.

FIG. 9 is a schematic illustration of embodiments of multi-mode sensors 300 that contain multiple regions of sensing 310 whereby each region 310 is capable of multi-mode sensing in accordance with disclosed embodiments. For example, region (a) may detect angular displacement ($\Theta_1$) and stretch (e.g., strain) simultaneously, region (b) may detect angular displacement ($\Theta_2$) and stretch (e.g., strain) simultaneously, and region (c) may detect angular displacement ($\Theta_3$) and stretch (e.g., strain) simultaneously. Such an embodiment may be part of a glove or the like to detect motion of a hand or fingers as disclosed above in connection with FIG. 4. Of course, other embodiments, multi-mode regions 310, and parameters sensed are also possible.

Figure 10:
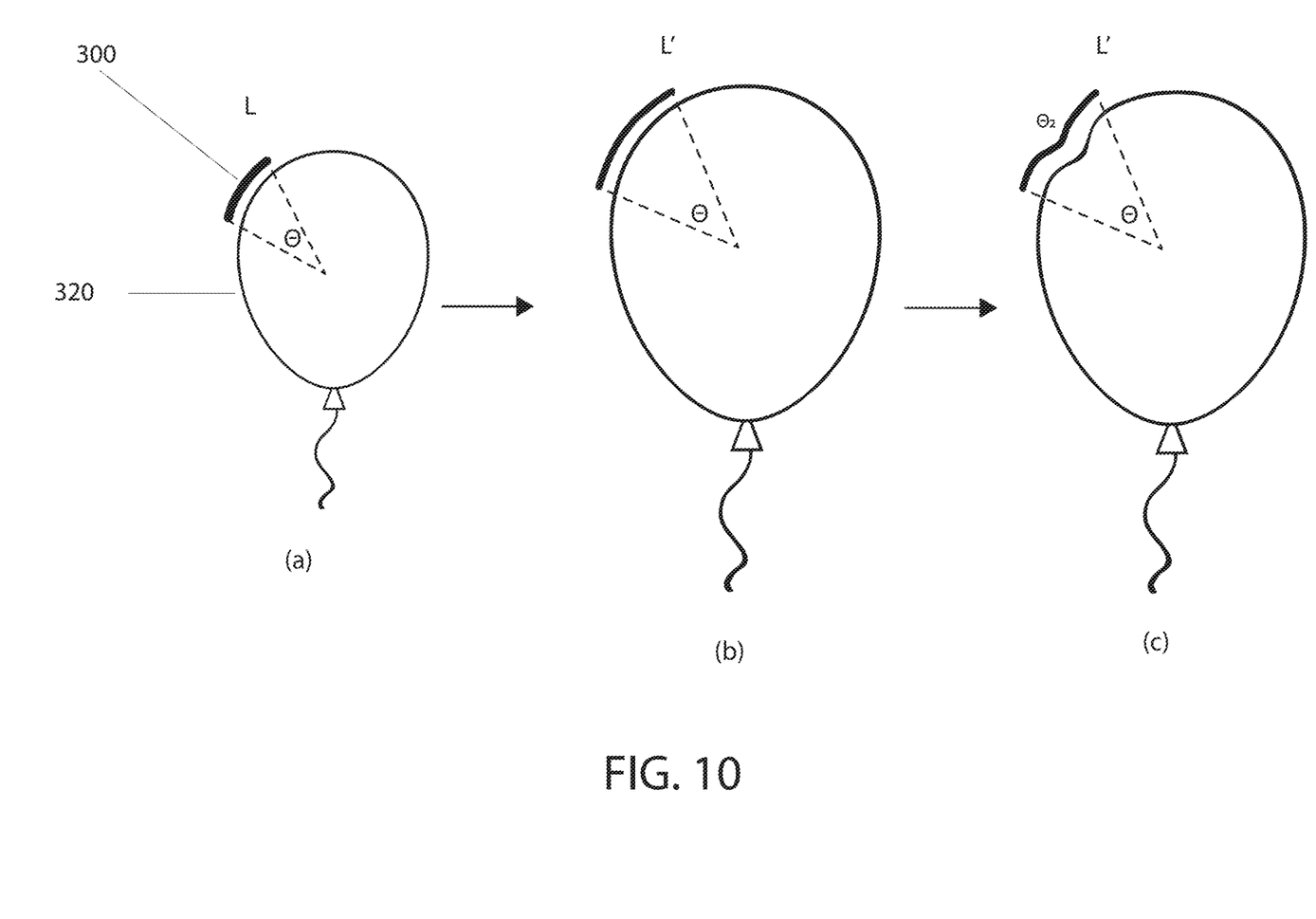
FIG. 10 is a schematic illustration of an extensible deformable substrate or structure with a multi-mode sensor attached in accordance with disclosed embodiments.

FIG. 10 is a schematic illustration of an extensible deformable substrate or structure 320 with a multi-mode sensor 300 attached in accordance with disclosed embodiments. As shown at FIG. 10($a$), an extensible deformable substrate 320 (e.g., a balloon or the like) may be configured with a multi-mode sensor 300 attached. If the circumference of the balloon/substrate 320 grows or shrinks in size there will be a corresponding change Length (L') of the sensor as seen in FIG. 10($b$) which will register a change in total strain/stretch. In FIG. 10($c$) a deformation is introduced into the circumference of the balloon/substrate 320 thereby inducing a change in angular displacement ($\Theta2$) of the sensor 300 with new Length (L'). Other configurations and measurements are also possible.

Although various embodiments have been shown and described, the present disclosure is not so limited and will be understood to include all such modifications and variations would be apparent to one skilled in the art.

What is claimed is:

1. A multi-mode sensor system comprising:
 a first attachment region;
 a first sense region having a first side located adjacent to the first attachment region;
 a second attachment region located adjacent to a second side of the first sense region;
 a second sense region located adjacent to the second attachment region on another side of the second attachment region; and
 an interface device comprising a calculation circuit that adds signals from the first sense region and the second sense region to measure a first parameter at a first time and takes a difference between the signals from the first sense region and the second sense region to measure a second parameter at the first time.

2. The multi-mode sensor system of claim 1 wherein the first and second sense region comprise a first material and the first and second attachment region comprise a second material different that the first material.

3. The multi-mode sensor system of claim 2 wherein the first material comprises an elastomeric matrix.

4. The multi-mode sensor system of claim 1 wherein in first and second sense region further comprise compliant capacitors.

5. The multi-mode sensor system of claim 1 wherein the first and second parameters are different physical parameters.

6. The multi-mode mode sensor system of claim 5 wherein the first parameter is an angular displacement and the second parameter is a force.

7. A system for analyzing data relative to sensed parameters, the system comprising:
 a sensor system comprising
  a first sense region configured to sense a first physical parameter; and
  a second sense region configured to sense a second physical parameter;
 an interface device further comprising:
  a user interface;
  a measurement circuit in communication with the sensor system; and a microcontroller comprising:
a calculation circuit in communication with the measurement circuit that adds signals from the first sense region and the second sense region to measure the first physical parameter at a first time and takes a difference between the signals from the first sense region and the second sense region to measure the second physical parameter at the first time; and
a memory comprising control and analysis software in communication with the calculation circuit that analyzes and stores data related to the first and second physical parameters.

8. The system for analyzing data relative to sensed parameters of claim 7 further comprising:
a remote device comprising a display for displaying the data related to the first and second physical parameters.

9. The system for analyzing data relative to sensed parameters of claim 7 further comprising:
a biofeedback device to provide a user with an indication that a predetermined condition has been reached related to at least one of the first and second physical parameters.

10. The system for analyzing data relative to sensed parameters of claim 7 wherein the sensor system further comprises at least one compliant capacitor.

11. The system for analyzing data relative to sensed parameters of claim claim 7 wherein the first and second physical parameters comprise different physical parameters.

12. The system for analyzing data relative to sensed parameters of claim 7 wherein the sensor system further comprises:
a compliant capacitor that communicates changes in capacitance due to deformation to the measurement circuit.

13. The system for analyzing data relative to sensed parameters of claim 12 wherein the compliant capacitor further comprises an elastomeric material.

14. The system for analyzing data relative to sensed parameters of claim 12 wherein the compliant capacitor measures angular displacement.

15. A multi-mode sensor that measures more than one parameter at the same time, the multi-mode sensor comprising:
a first strain transformation structure;
a first sensor beneath the first transformation structure;
an offset region beneath the first sensor;
a second sensor beneath the offset region; and
an interface device comprising a calculation circuit that adds signals from the first sensor and the second sensor to measure a first parameter at a first time and takes a difference between the signals from the first sensor and the second sensor to measure a second parameter at the first time.

16. The multi-mode sensor of claim 15 further comprising a second strain transformation structure beneath the second sensor.

17. The multi-mode sensor of claim 15 wherein the first sensor and the second sensor comprise capacitive sensors.

18. The multi-mode mode sensor of claim 17 wherein the difference in capacitive measurement between the first sensor and the second sensor measures an angular displacement parameter.

19. The multi-mode mode sensor of claim 17 wherein the added capacitive measurement between the first sensor and the second sensor measures a force parameter.

20. The multi-mode mode sensor of claim 17 wherein the added capacitive measurement between the first sensor and the second sensor measures a strain parameter.

21. The multi-mode sensor of claim 16 further comprising:
a first axis about which the first transformation structure, the first sensor, the second sensor, and the second transformation structure are substantially aligned;
a third strain transformation structure substantially aligned with a second axis that is substantially orthogonal to the first axis;
a third sensor adjacent to the third transformation structure and substantially aligned with the second axis;
a second offset region adjacent to the third sensor;
a fourth sensor adjacent to the second offset region and substantially aligned with the second axis; and
a fourth strain transformation structure adjacent to the fourth sensor and substantially aligned with the second axis.

22. The multi-mode sensor of claim 21 wherein the first sensor, the second sensor, the third sensor, and the fourth sensor are configured to measure different physical parameters.

23. The multi-mode sensor of claim 21 further comprising:
a fifth strain transformation structure substantially aligned with a third axis that is substantially orthogonal to both the first axis and the second axis;
a fifth sensor adjacent to the fifth transformation structure and substantially aligned with the third axis;
a third offset region adjacent to the fifth sensor;
a sixth sensor adjacent to the third offset region and substantially aligned with the third axis; and
a sixth strain transformation structure adjacent to the sixth sensor and substantially aligned with the third axis.

24. The multi-mode sensor of claim 23 wherein the first sensor, the second sensor, the third sensor, the fourth sensor, the fifth sensor, and the sixth sensor are configured to measure different physical parameters.

25. A multi-mode sensor comprising:
an elastomeric strand comprising:
a first multi-mode sensing region configured to sense at least two different physical parameters;
a second multi-mode sensing region, space apart from the first multi-mode sensing region, and configured to sense at least two different physical parameters; and
an interface device comprising a calculation circuit that adds signals from the first multi-mode sensing region and the second multi-mode sensing region to measure a first parameter at a first time and takes a difference between the signals from the first multi-mode sensing region and the second multi-mode sensing region to measure a second parameter at the first time.

26. The multi-mode sensor of claim 25 wherein the the two different physical parameters comprise angular displacement and strain.

* * * * *

UNITED STATES PATENT AND TRADEMARK OFFICE
CERTIFICATE OF CORRECTION

PATENT NO. : 11,690,531 B2
APPLICATION NO. : 17/061163
DATED : July 4, 2023
INVENTOR(S) : Colton A. Ottley et al.

It is certified that error appears in the above-identified patent and that said Letters Patent is hereby corrected as shown below:

In the Claims

Claim 11 should read:
11. The system for analyzing data relative to sensed parameters of claim 7 wherein the first and second physical parameters comprise different physical parameters.

Claim 26 should read:
26. The multi-mode sensor of claim 25 wherein the two different physical parameters comprise angular displacement and strain.

Signed and Sealed this
Thirtieth Day of January, 2024

*Katherine Kelly Vidal*

Katherine Kelly Vidal
*Director of the United States Patent and Trademark Office*